United States Patent
Du et al.

(10) Patent No.: US 11,891,379 B2
(45) Date of Patent: Feb. 6, 2024

(54) DEUTERATED DEFACTINIB COMPOUND AND USE THEREOF

(71) Applicant: HINOVA PHARMACEUTICALS INC., Sichuan (CN)

(72) Inventors: Wu Du, Sichuan (CN); Yu Li, Sichuan (CN); Kun Wen, Sichuan (CN); Xinghai Li, Sichuan (CN); Yuanwei Chen, Sichuan (CN)

(73) Assignee: HINOVA PHARMACEUTICALS INC., Sichuan (CN)

( * ) Notice: Subject to any disclaimer, the term of this patent is extended or adjusted under 35 U.S.C. 154(b) by 680 days.

(21) Appl. No.: 17/054,080

(22) PCT Filed: May 6, 2019

(86) PCT No.: PCT/CN2019/085722
§ 371 (c)(1),
(2) Date: Nov. 9, 2020

(87) PCT Pub. No.: WO2019/214587
PCT Pub. Date: Nov. 14, 2019

(65) Prior Publication Data
US 2021/0238166 A1 Aug. 5, 2021

(30) Foreign Application Priority Data
May 7, 2018 (CN) .......................... 201810427571.1

(51) Int. Cl.
*A61K 31/506* (2006.01)
*C07D 403/12* (2006.01)

(52) U.S. Cl.
CPC ........ *C07D 403/12* (2013.01); *C07B 2200/05* (2013.01)

(58) Field of Classification Search
CPC .................................................... A61K 31/506
USPC ........................................... 514/255, 252.13
See application file for complete search history.

(56) References Cited

U.S. PATENT DOCUMENTS

2011/0053968 A1   3/2011   Zhang

FOREIGN PATENT DOCUMENTS

| CN | 106146406 A | 11/2016 |
|---|---|---|
| WO | 2008129380 A1 | 10/2008 |
| WO | 2010144499 A2 | 12/2010 |

OTHER PUBLICATIONS

Zhang, Yinsheng; Development of Deuterated Drugs: Past, Present and Future; Progress in Pharmaceutical Sciences; vol. 41, No. 12, Dec. 31, 2017, pp. 902-918.

*Primary Examiner* — Raymond J Henley, III
(74) *Attorney, Agent, or Firm* — NKL Law; Allen Xue

(57) ABSTRACT

This disclosure provides a compound as shown in formula (I) or optical isomers, pharmaceutically acceptable salts, hydrates or solvates thereof. In formula (I), R1-R18 are independently selected from hydrogen and deuterium respectively, but not all are hydrogen at the same time. The compound and salts, hydrates or solvates thereof can be used as FAK inhibitors, and used in the preparation of anti-cancer drugs, and compared with the undeuterated control compound Defactinib, the compound has significantly improved metabolic stability and pharmacokinetic properties.

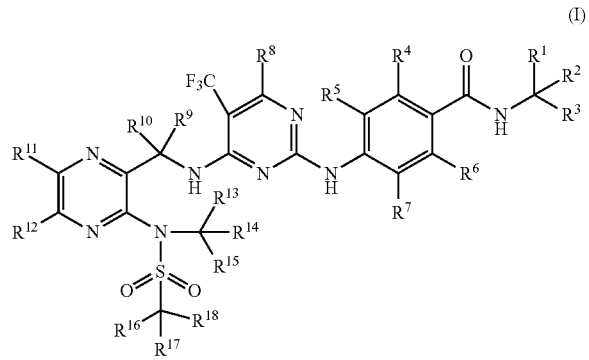

12 Claims, No Drawings

DEUTERATED DEFACTINIB COMPOUND AND USE THEREOF

TECHNICAL FIELD

The present invention relates to deuterated defactinib compounds and the use thereof.

BACKGROUND ART

Defactinib (VS-6063), developed by Verastem Oncology company, is a selective and orally effective FAK inhibitor, has a structure

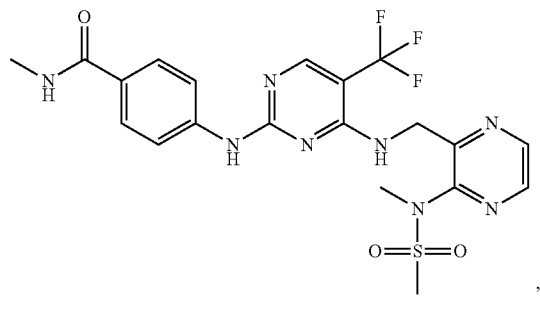 [SMILES: CNC(=O)c1ccc(Nc2ncc(C(F)(F)F)c(NCc3nccnc3N(C)S(C)(=O)=O)n2)cc1]

and is currently undergoing clinical trials.

Deuterated drugs denote the replacement of part of the hydrogen atoms in drug molecules with deuterium. Because the shape and volume of deuterium in the drug molecule are very close to hydrogen, the deuterated drug will retain the in vitro biological activity and selectivity of original drug. Since C-D bond is more stable than C—H bond, C—D bond is less likely to be broken during the metabolic reaction of deuterated drugs, and the half-life may be prolonged.

However, due to the complex metabolic processes in biological system, the pharmacokinetic properties of drugs in organisms are influenced by many factors, and also exhibit corresponding complexity. Compared with the corresponding non-deuterated drugs, the changes in the pharmacokinetic properties of deuterated drugs show unpredictability and is largely by chance. Deuteration at certain sites not only cannot prolong the half-life, but may shorten it (Scott L. Harbeson, Roger D. Tung. Deuterium in Drug Discovery and Development, P405-406.) and deteriorate its pharmacokinetic properties; on the other hand, it is also extremely difficult to replace hydrogen at certain positions of the drug molecule with deuterium. Therefore, the position in a drug molecule that is suitable for deuteration is not obvious, and the deuteration effect is also unpredictable.

Therefore, defactinib molecule was deuterated to obtain a class of deuterated drugs with better pharmacokinetic properties, reduced dosage, and reduced toxic and side effects of metabolites, and that is essential for obtaining more effective and safer new drugs.

Content of the Invention

The object of the present invention is to provide an effective and safe new drug for treatment of cancer, having better metabolic stability and pharmacokinetic properties.

The present invention first provides compound of formula (I) or the optical isomer, the pharmaceutically acceptable salt, the hydrate or the solvate thereof:

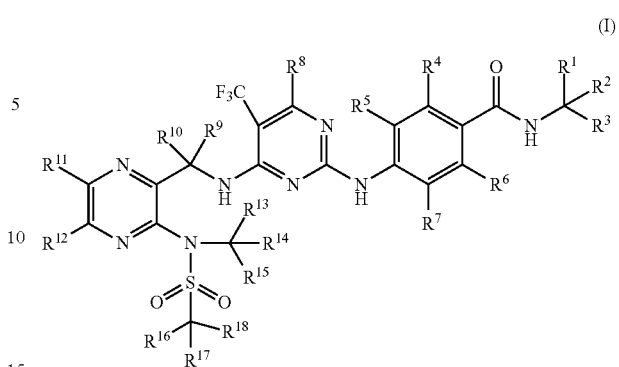

Wherein, $R^1$-$R^{18}$ are each independently selected from hydrogen and deuterium, and not all of them are hydrogen.

Further, the compound has the structure of formula (II):

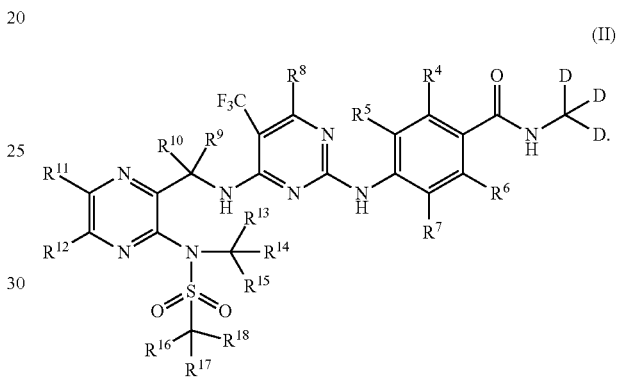

Further, the compound has the structure of formula (III):

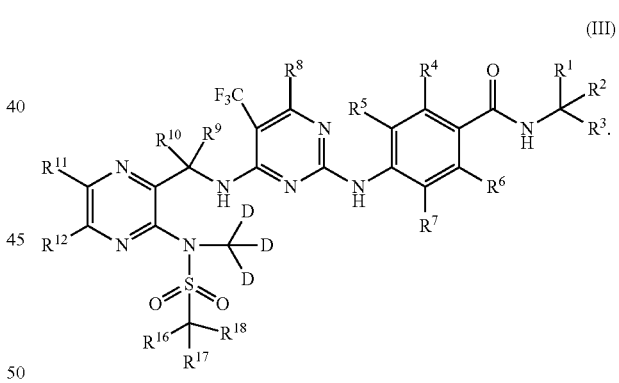

Further, the compound has the structure of formula (IV):

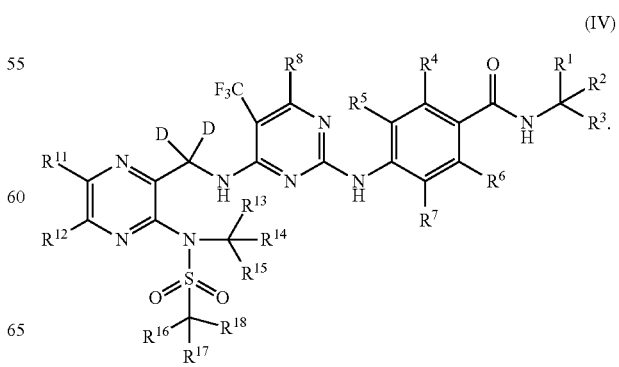

Further, the compound has the structure of formula (V):
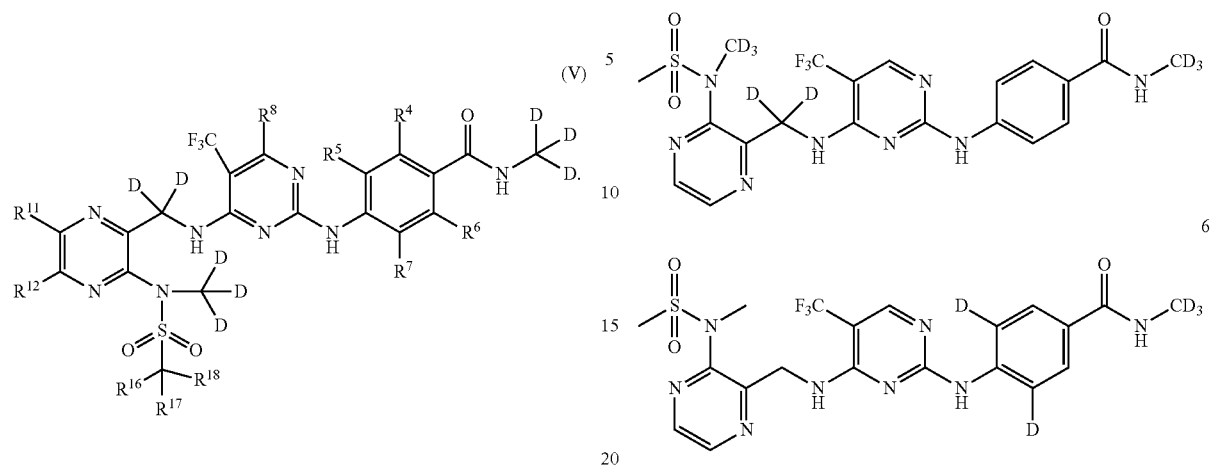
Further, the compound is one of the following compounds:
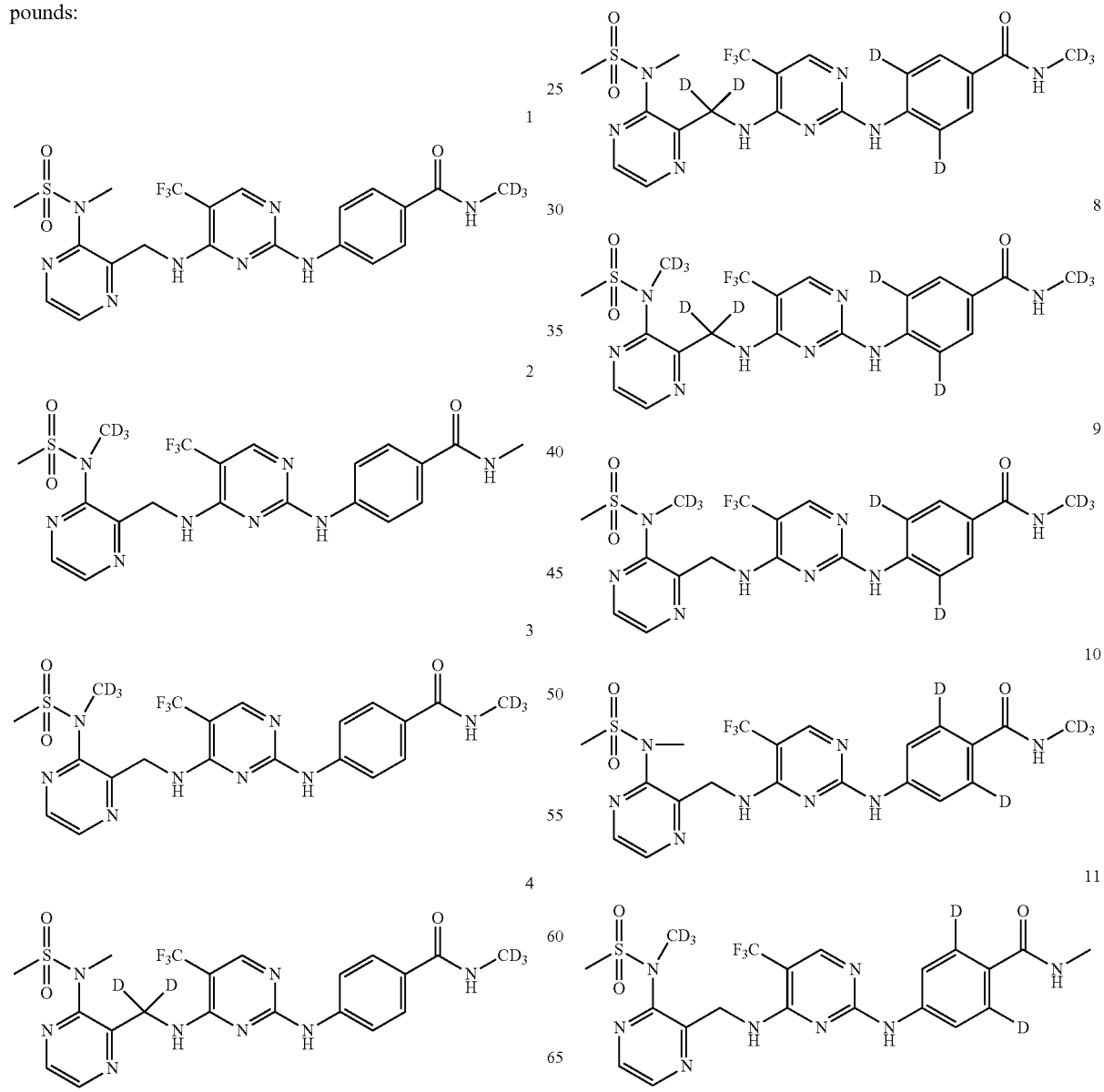

12

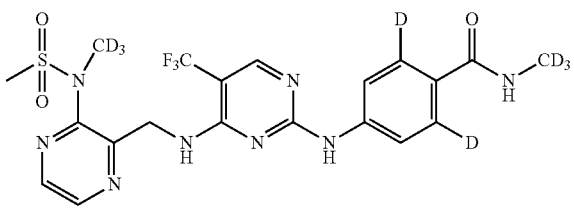

13

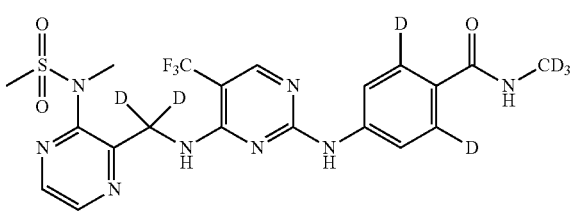

14

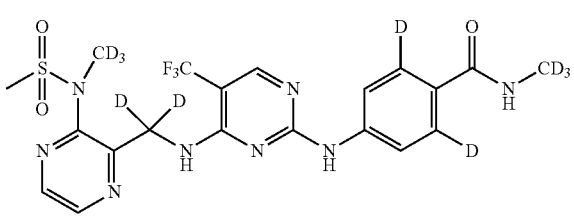

15

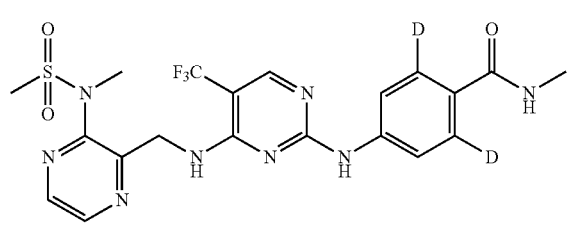

16

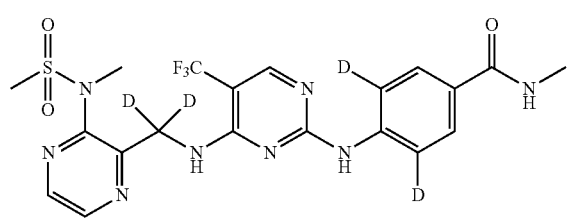

17

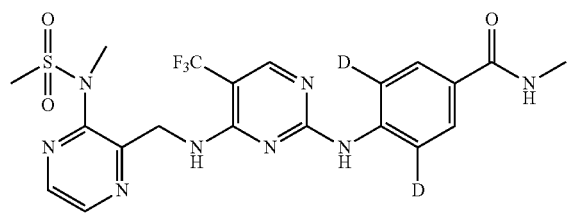

18

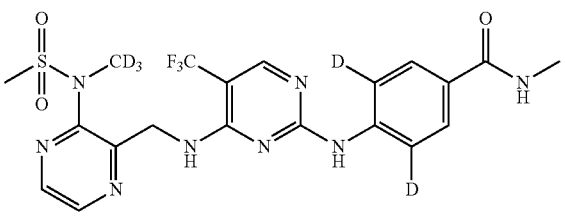

Further, the pharmaceutically acceptable salt is phosphate, d-camphorsulfonate, hydrochloride, hydrobromide, hydrofluoride, sulfate, nitrate, formate, acetate, propionate, oxalate, malonate, succinate, fumarate, maleate, lactate, malate, tartrate, citrate, picrate, methanesulfonate, besylate, benzenesulfonate, aspartate or glutamate of the compound, and preferably hydrochloride of the compound.

The present invention further provides the use of above compound or the optical isomer, the pharmaceutically acceptable salt, the hydrate or the solvate thereof in the preparation of drugs for treatment of cancers.

Further, the cancer is selected from pancreatic cancer, solid tumor, non-small cell lung cancer, mesothelioma, and ovarian cancer.

The present invention further provides the use of above compound a or the optical isomer, the pharmaceutically acceptable salt, the hydrate or the solvate thereof in the preparation of FAK inhibitors.

The present invention further provides a drug for treatment of cancer, that is a preparation obtained by using the compound mentioned above or the optical isomer, the pharmaceutically acceptable salt, the hydrate or the solvate as active ingredients, with addition of pharmaceutically acceptable excipients.

Experiments have proved that the compounds provided in the present invention and their salts, hydrates or solvates can be used as FAK inhibitors for the preparation of anti-cancer drugs, and compared with the non-deuterated control compound defactinib, the metabolic stability and pharmacokinetic properties of the compound according to the present invention are significantly improved, and the application prospects are excellent.

As used herein, "deuterated" means the replacement of one or more hydrogens in a compound or a group with deuterium. Deuteration can be mono-, di-, poly-, or fully-substituted. In another preferred example, the deuterium isotope content at the deuterium substitution position is more than the natural deuterium isotope content (0.015%), preferably more than 50%, preferably more than 75%, preferably more than 95%, preferably more than 97%, preferably more than 99%, and preferably more than 99.5%.

As used herein, the term "compound of the present invention" means the compound of formula (I). The term also includes various optical isomers, pharmaceutically acceptable salts, hydrates or solvates of the compound of formula (I).

As used herein, the term "pharmaceutically acceptable salt" means the pharmaceutically acceptable salts formed by a compound of the present invention and an acid or base. Pharmaceutically acceptable salts include inorganic salts and organic salts. A preferred class of salts are those formed by the compounds of the present invention and acids. Acids suitable for salt formation include but are not limited to: phosphoric acid, D-camphorsulfonic acid, hydrochloric acid, hydrobromic acid, hydrofluoric acid, sulfuric acid, nitric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, benzenesulfonic acid, aspartic acid or glutamic acid.

Further, the acid forming the pharmaceutically acceptable salt is hydrochloric acid.

The pharmaceutically acceptable excipients described herein have certain physiological activities, but the addition of the ingredients will not change the dominant position of the above-mentioned pharmaceutical composition in the course of disease treatment, but only exert auxiliary functions. These auxiliary functions are only the use of the known activity of the ingredients, that is a commonly used auxiliary treatment in the medical field. If the aforementioned auxiliary components are used in conjunction with the pharmaceutical composition of the present invention, they should still fall within the protection scope of the present invention.

Obviously, based on above content of the present invention, according to the common technical knowledge and the conventional means in the field, without departure from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

The starting materials and equipment used in the present invention are all known products and can be obtained by purchasing commercially available products.

In the following, the compound of the present invention is prepared by the route mentioned in synthetic method 1 or 2:

Synthetic method 1

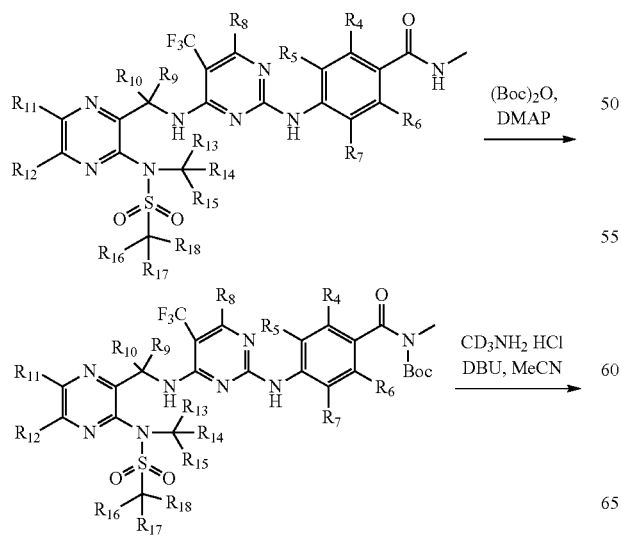

Synthetic method 2

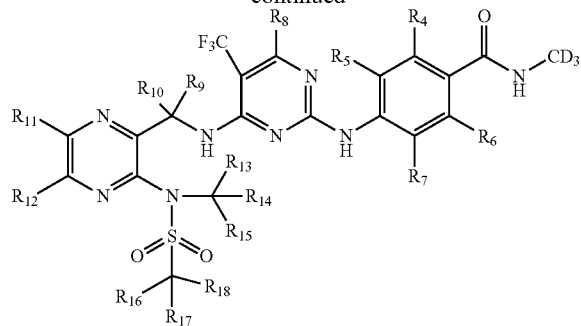

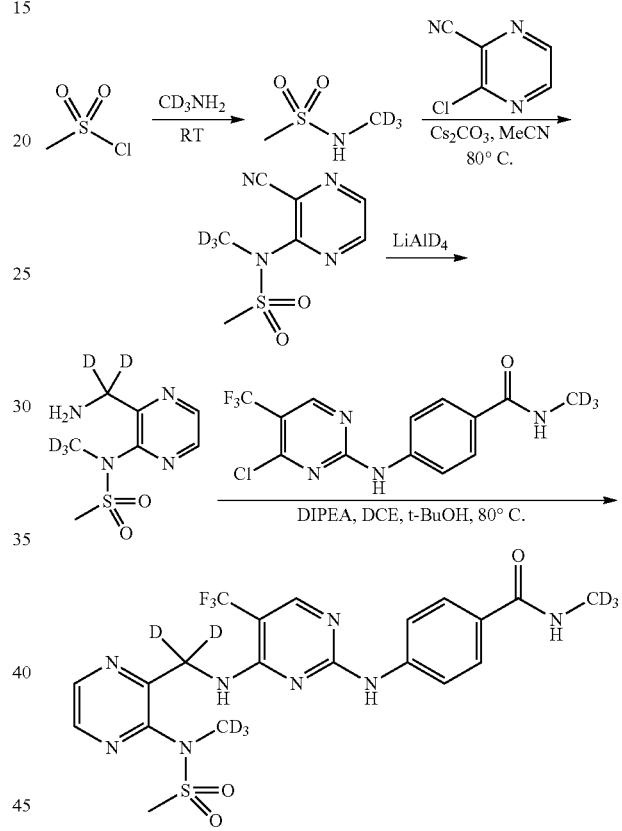

Example 1

Synthesis of N-(trideuteromethyl)-4-((4-(((3-(N-methylmethylsulfonyl)pyrazin-2-yl)methyl)amino)-5-(trifluoromethyl)pyrimidin-2-yl)amino)benzamide (compound 1)

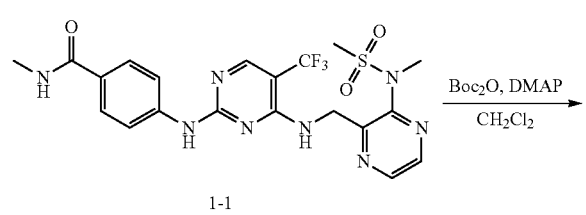

1-1

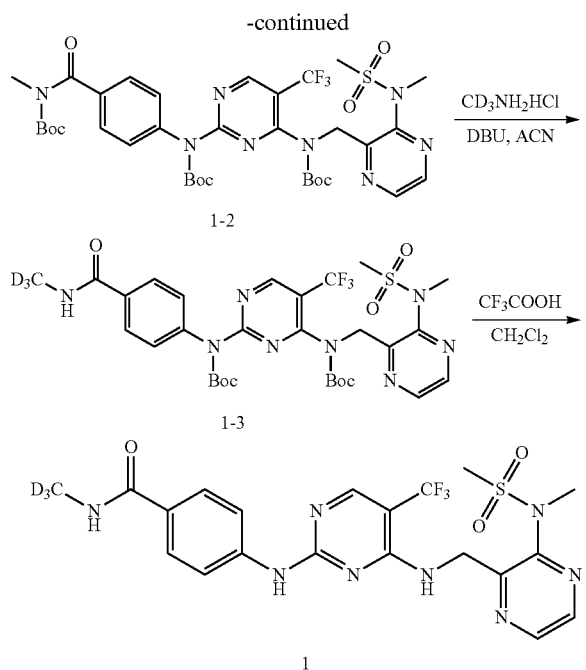

The crude product was separated by column chromatography, to obtain t-butyl (4-((t-butoxycarbonyl)(4-((t-butoxycarbonyl) ((3-(N-methylmethanesulfonamido)pyrazin-2-yl)methyl)amino)-5-(trifluoromethyl)pyrimidin-2-yl)a mino) benzoyl)(methyl)carbamate (136.0 mg, yield 42.8%) as off-white solid. MS (ESI) m/z 811.2 [M+H]$^+$.

(2) Synthesis of Compound t-butyl (4-((t-butoxycarbonyl)((3-(N-methylmethanesulfonamido) pyrazin-2-yl)methyl)amino)-5-(trifluorom ethyl) pyrimidin-2-yl)(4-(methylcarbamoyl)phenyl) carbamate

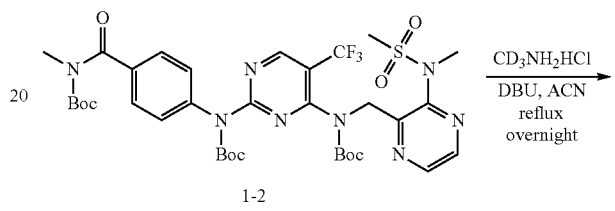

(1) Synthesis of Compound t-butyl (4-((t-butoxycarbonyl)(4-((t-butoxycarbonyl)((3-(N-methylmethanesulfonamido)pyrazin-2-yl)methyl)amino)-5-(trifluoromethyl)pyrimidin-2-yl)amino)b enzoyl) (methyl)carbamate

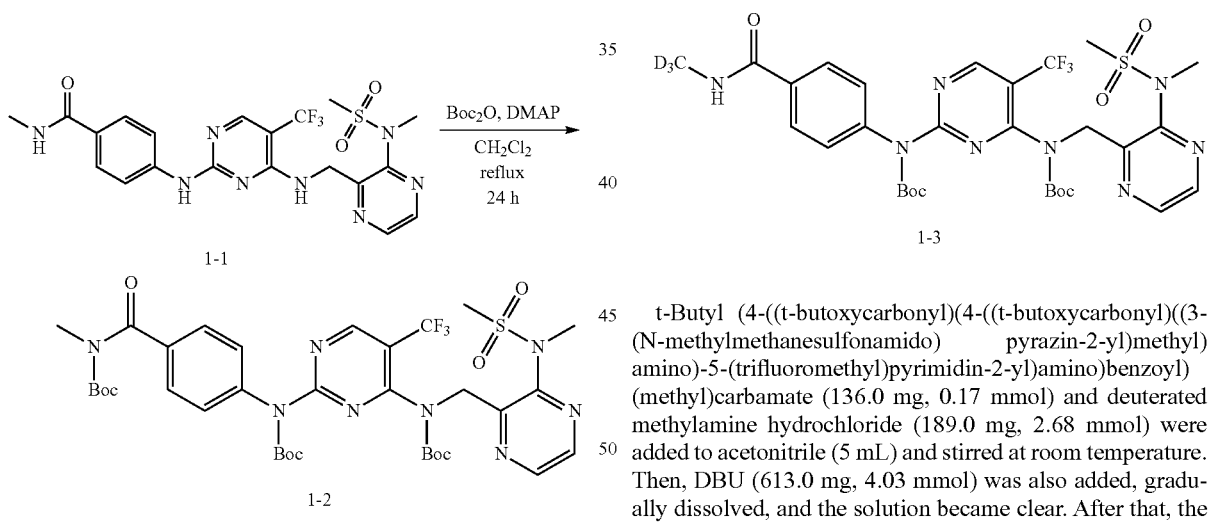

N-methyl-4-((4-(((3-(N-methylmethylsulfonyl)pyrazin-2-yl)methyl)amino)-5-(trifluoromethyl)pyrim idin-2-yl) amino)benzamide (200.0 mg, 0.39 mmol; namely compound 1-1, purchased from Chengdu Henghui Chemical Pharmaceutical Technology Co., Ltd.) and DMAP (1.3 g, 10.57 mmol) were dissolved in dichloromethane (10 mL), and then (Boc)$_2$O (1.7 g, 7.83 mmol)) was drop added. The reaction mixture was refluxed for 24 h in an oil bath at 45° C. On the next day, the reaction was cooled to room temperature, to which were added dichloromethane and HCl (0.1 M) solution, and extracted, then stood to separate the layers. The organic phase was washed with saturated brine, dried with anhydrous sodium sulfate, vacuum filtered, and rotatory evaporated to remove the solvent.

t-Butyl (4-((t-butoxycarbonyl)(4-((t-butoxycarbonyl)((3-(N-methylmethanesulfonamido) pyrazin-2-yl)methyl) amino)-5-(trifluoromethyl)pyrimidin-2-yl)amino)benzoyl) (methyl)carbamate (136.0 mg, 0.17 mmol) and deuterated methylamine hydrochloride (189.0 mg, 2.68 mmol) were added to acetonitrile (5 mL) and stirred at room temperature. Then, DBU (613.0 mg, 4.03 mmol) was also added, gradually dissolved, and the solution became clear. After that, the reaction mixture was refluxed overnight in an oil bath. On the next day, the reaction was cooled to room temperature, and rotatory evaporated to remove the solvent, to which were added dichloromethane and HCl solution (0.1 M), vigorously stirred, then stood to separate the layers. The organic phase was washed with pure water and saturated brine, respectively, dried with anhydrous sodium sulfate, and rotatory evaporated to remove the solvent. The crude product was separated and purified by Pre-TLC (PE/EA=2:1), to obtain t-butyl (4-((t-butoxycarbonyl)((3-(N-methylmethanesulfonamido)pyrazin-2-yl)methyl)amino)-5-(trifluorom ethyl)pyrimidin-2-yl)(4-(methylcarbamoyl)phenyl) carbamate (42.0 mg, yield 35.3%) as white solid. MS (ESI) m/z 614.2 [M+H]$^+$.

(3) Synthesis of Compound N-(trideuteromethyl)-4-((4-(((3-(N-methylmethylsulfonyl) pyrazin-2-yl)methyl)amino)-5-(trifluoromethyl)pyrimidin-2-yl)amino)benzamide (compound 1)

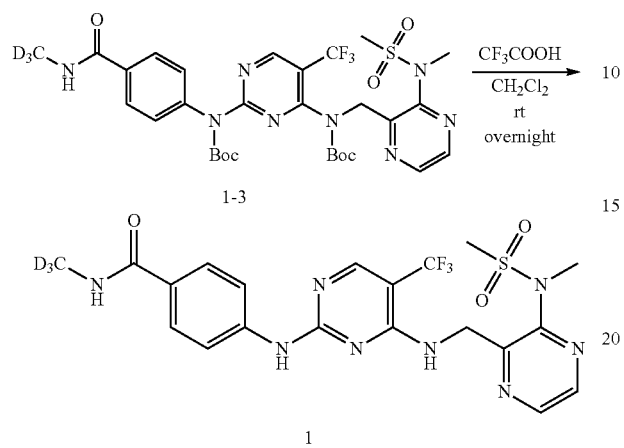

t-Butyl (4-((t-butoxycarbonyl)((3-(N-methylmethanesulfonamido)pyrazin-2-yl)methyl)amino)-5-(trifluoromethyl)pyrimidin-2-yl)(4-(methylcarbamoyl)phenyl)carbamate (42.0 mg, 0.06 mmol) was dissolved in dichloromethane (2 mL), and stirred at room temperature (failed to dissolve and become clear), to which was then added trifluoroacetic acid (0.1 mL). The reaction mixture gradually became clear, and allowed to react overnight at room temperature under stirring. On the next day, the reaction was rotatory evaporated to remove the solvent, to which were added ethyl acetate and saturated NaHCO₃ solution, and the mixture was vigorously stirred, then stood to separate the layers. pH value of water phase was detected to be about 7-8. The organic phase was washed with water and saturated brine twice, respectively, dried with anhydrous sodium sulfate, and rotatory evaporated to remove the solvent, to obtain N-deuteromethyl-4-((4-(((3-(N-methylmethylsulfonyl)pyrazin-2-yl)methyl)amino)-5-(trifluoromethy 1)pyrimidin-2-)amino)benzamide as off-white solid (24.0 mg, yield 80.0%). MS (ESI) m/z 514.2 [M+H]⁺.

$^1$H NMR (400 MHz, DMSO-$d_6$): δ 9.86 (s, 1H), 8.69 (d, J=2.4 Hz, 1H), 8.58 (d, J=2.8 Hz, 1H), 8.32 (s, 1H), 8.18 (s, 1H), 7.67-7.59 (dd, J=19.6, 8.8 Hz, 4H), 7.48-7.45 (t, J=5.2 Hz, 1H), 5.00 (d, J=4.8 Hz, 2H), 3.22 (s, 3H), 3.20 (s, 3H).

Example 2 Synthesis of N-methyl-4-((4-(((3-(N-deuteromethylmethanesulfonamido) pyrazin-2-yl)methyl)amino)-5-(trifluoromethyl)pyrimidin-2-yl)amino)benzamide (compound 2)

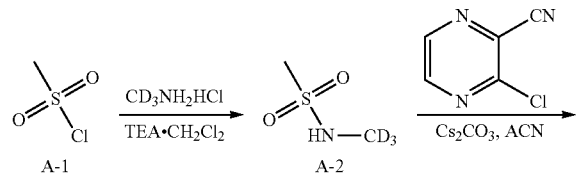

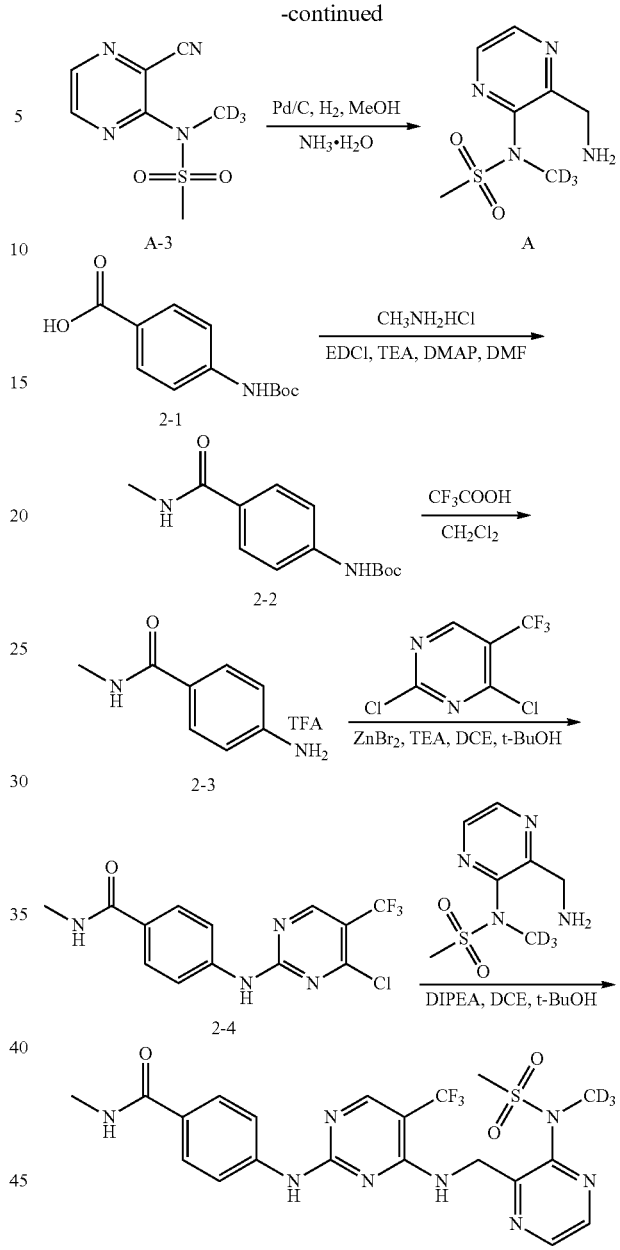

(1) Synthesis of Compound N-deuteromethylmethanesulfonamide

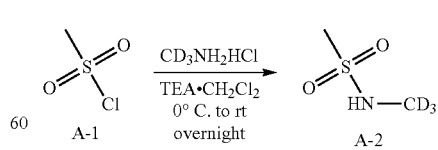

Methylsulfonyl chloride (3.0 g, 26.19 mmol) was weighed and placed in a 100 mL single-neck round bottom flask, to which was added dichloromethane (30 mL), and then stirred to make the solution become clear at room temperature. Then, the system was moved to an ice water bath to continue cooling and stirring. After 15 min, triethylamine (6.1 g, 60.24 mmol) was slowly added to the system. After addition, the system was still stirred for 10 min under insulation. Then, deuterated methylamine hydrochloride (2.0 g, 28.81 mmol) was slowly added to the system in batches. After that, the ice bath was removed, and the system was warmed to room temperature and reacted overnight under stirring. On the next day, once the reaction was completed by monitoring, the solvent was removed by rotary evaporation, and ethyl acetate (30 mL) was further added to the system. The reaction was stirred for 10 min, and subjected to suction filtration, then the filter cake was rinsed with a small amount of ethyl acetate. The filtrate was combined and concentrated under reduced pressure to obtain the crude product, that was then separated by column chromatography to obtain N-deuteromethylmethanesulfonamide as colorless transparent oily liquid (2.1 g, yield 71.4%).

(2) Synthesis of Compound N-(3-cyanopyrazin-2-yl)-N-deuteromethylmethanesulfonamide

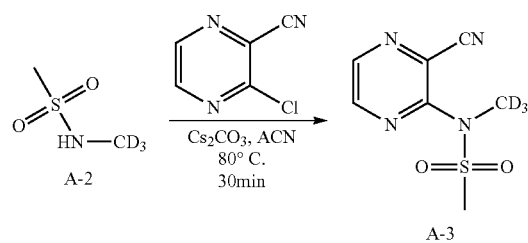

3-Chloropyrazin-2-nitrile (1.7 g, 12.48 mmol) was weighed and placed in a 100 mL single-neck round bottom flask, to which was added 40 mL acetonitrile, and stirred to make the solution become clear at room temperature. Then, cesium carbonate (8.1 g, 24.96 mmol) was slowly added to the system in batches. After addition, the solution of N-deuteromethylmethanesulfonamide (2.1 g, 18.72 mmol) in acetonitrile (10 mL) was drop added to the system. After that, the system was transferred to an oil bath at 80° C. to reflux and react under stirring. After 30 min, the complete consumption of raw materials was detected by TLC. The oil bath was removed, and the system was allowed to cool to room temperature, then suction filtration was performed. The filter cake was rinsed with acetonitrile (100 mL) several times. The filtrate was combined, and the solvent was removed by rotary evaporation to obtain a crude product, which was then separated by column chromatography to obtain N-(3-cyanopyrazin-2-yl)-N-deuteromethylmethanesulfonamide as light brown oily liquid (1.1 g, yield 42.3%). MS (ESI) m/z 233.1 [M+H$_2$O]$^+$.

$^1$H NMR (400 MHz, CDCl$_3$) δ 8.65-8.63 (dd, J=6.0, 2.4 Hz, 2H), 3.26 (s, 3H).

(3) Synthesis of Compound N-(3-(aminomethyl)pyrazin-2-yl)-N-deuteromethylmethanesulfonamide

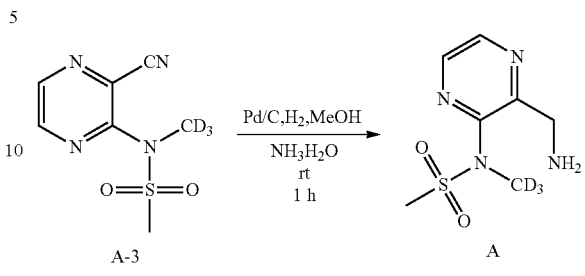

N-(3-cyanopyrazin-2-yl)-N-deuteromethylmethanesulfonamide (42 mg, 0.20 mmol) was weighed and placed in a 25 mL single-neck round bottom flask, to which were added 4 mL methanol and 1 mL ammonia solution, and stirred at room temperature. Then, wet palladium carbon (10.0 mg) was added to the system, and the system was subjected to hydrogen replacement operation, which was repeated ten times. After that, the system was stirred and reacted at room temperature. After 1 h, the reaction was completed by detection. The system was subjected to suction filtration, and the filter cake was rinsed with methanol (25 mL) several times in small amounts. The filtrate was combined, concentrated under reduced pressure to remove the solvent, and the residual water in the system was removed by repeated evaporation with methanol to obtain N-(3-(aminomethyl)pyrazin-2-yl)-N-deuteromethylmethanesulfonamide as light yellow-brown oily liquid, which was directly used in the next step without further purification. MS (ESI) m/z 220.1 [M+H]$^+$.

(4) Synthesis of Compound t-butyl (4-(methylcarbamoyl)phenyl)carbamate

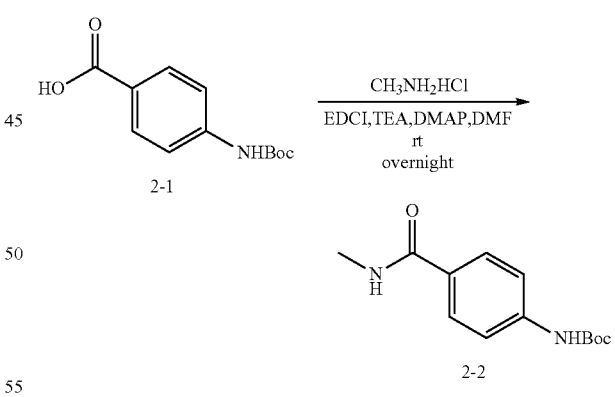

4-((t-Butoxycarbonyl)amino)benzoic acid (3.0 g, 12.65 mmol) was weighed and placed in a 250 mL single-neck round bottom flask, to which was added 50 mL DMF, and stirred at room temperature. Then, EDCI (4.8 g, 25.29 mmol), TEA (4.5 g, 44.28 mmol), methylamine hydrochloride (1.3 g, 18.98 mmol), and DMAP (16.0 mg, 0.13 mmol) were sequentially added to the system. After that, the system was stirred and reacted overnight at room temperature. On the next day, when raw materials disappeared by detection, ethyl acetate (70 mL) and water (50 mL) were added to the system. The mixture was stirred vigorously, and stood for layers separation. The aqueous phase was back-extracted with ethyl acetate (20 mL*3), and the organic layers were combined, washed respectively with water (20 mL*3) and saturated brine (30 mL), dried with anhydrous sodium sulfate. The solvent was removed by rotary evaporation to obtain a crude product, which was then separated by column chromatography to obtain t-butyl(4-(methylcarbamoyl)phenyl)carbamate as off-white solid (2.1 g, yield 66.5%). MS (ESI) m/z 251.2 [M+H]$^+$.

(5) Synthesis of Compound 4-amino-N-methylbenzamide trifluoroacetate

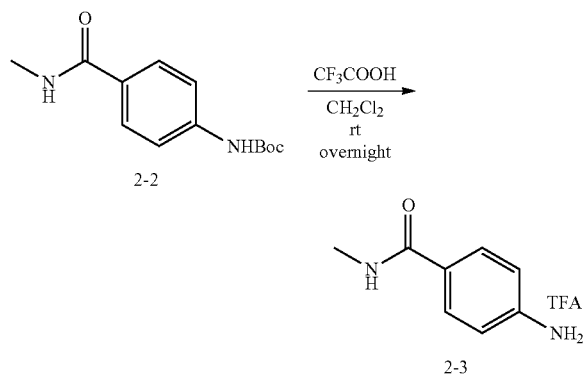

t-Butyl (4-(methylaminoformyl)phenyl)carbamate (500 mg, 2.00 mmol) was weighed and placed in a 50 mL single neck round bottom flask, to which was added dichloromethane (10 mL) and stirred at room temperature. Then, trifluoroacetic acid (1 mL) was added to the system. After addition, the system was stirred and reacted overnight at room temperature. On the next day, the reaction was completed by TLC detection. The reaction solution was concentrated to remove the solvent and excess trifluoroacetic acid, and the residual trifluoroacetic acid in the system was removed by multiple co-steaming with dichloromethane until the system was completely solidified, to obtain 4-amino-N-methylbenzamide trifluoroacetate (510 mg) as off-white solid, that was directly used in the next step without further purification.

(6) Synthesis of Compound 4-((4-chloro-5-(trifluoromethyl)pyrimidin-2-yl)amino)-N-methylbenzamide

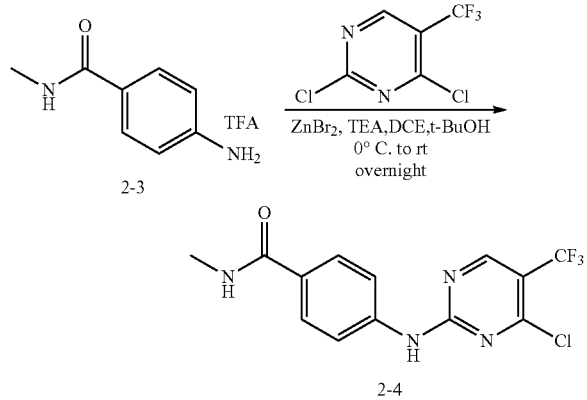

2,4-Dichloro-5-(trifluoromethyl)pyrimidine (499 mg, 2.30 mmol) was weighed and placed in a 50 mL single neck round bottom flask, to which were added 1,2-dichloroethane (5 mL) and t-butanol (5 mL), and stirred at room temperature to make the solution become clear. Then, the system was transferred in an ice-water bath to continue cooling and stirring. After 15 min, zinc bromide (1.4 g, 6.00 mmol) was added to the system. After addition, the system was still kept in the ice water bath and stirred for 30 min. Then, 4-amino-N-methylbenzamide trifluoroacetate and triethylamine (648 mg, 6.40 mmol) synthesized in the previous step were added to the system. After addition, the ice bath was removed, and the system was stirred and reacted overnight at room temperature. On the next day, the reaction was completed by detection, and after removing the solvent by rotary evaporation, ethyl acetate (30 mL) and water (20 mL) were added to the system. The reaction was stirred vigorously, and stood for layers separation. The aqueous layer was back-extracted with ethyl acetate (10 mL*3), and the organic phases were combined, washed successively with water (15 mL*3) and saturated brine (15 mL), dried with anhydrous sodium sulfate, and concentrated under reduced pressure to obtain a crude product, which was then separated by column chromatography to obtain 4-((4-chloro-5-(trifluoromethyl)pyrimidin-2-yl)amino)-N-methylbenzamide as off-white solid (280 mg, yield 42.3%). MS (ESI) m/z 331.0 [M+H]$^+$.

(7) Synthesis of Compound N-methyl-4-((4-(((3-(N-deuteromethylmethanesulfonamido) pyrazin-2-yl) methyl)amino)-5-(trifluoromethyl)pyrimidin-2-yl) amino)benzamide

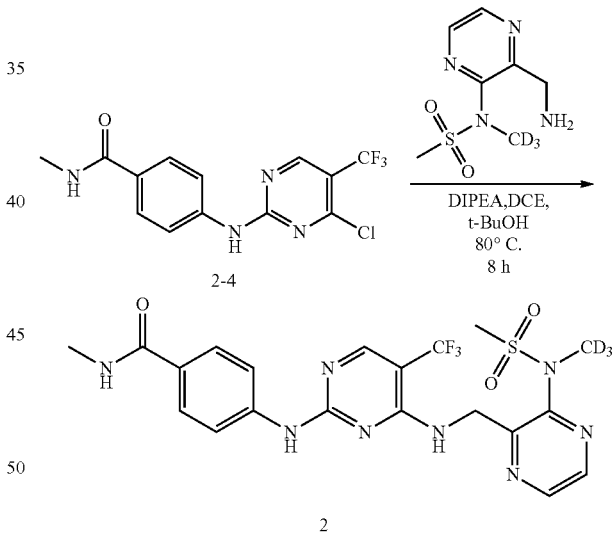

To a 25 mL single-neck round bottom flask containing N-(3-(aminomethyl)pyrazin-2-yl)-N-deuteromethylmethanesulfonamide (65.8 mg, 0.30 mmol), were added 1,2-dichloroethane (5 mL) and t-butanol (5 mL), and stirred at room temperature to make the solution become clear. Then, 4-((4-chloro-5-(trifluoromethyl)pyrimidin-2-yl)amino)-N-methylbenzamide (100.0 mg, 0.30 mmol) and diisopropylethylamine (116.3 mg, 0.90 mmol) were successively added to the system, and after addition, the system was transferred to an oil bath at 80° C. and refluxed for reaction. After 8 h, disappearance of raw materials was detected by TLC. After heating was removed, and the system was cooled to room temperature, the solvent was removed by rotary evaporation to obtain a crude product, which was then separated and purified by Prep-TLC to obtain N-methyl-4-((4-(((3-(N- deuteromethylmethanesulfonamido)pyrazin-2-yl)methyl)amino)-5-(trifluoromethyl)pyrimidin-2-yl)amino)benzamide as off-white solid (12 mg, yield 7.8%). MS (ESI) m/z 514.2 [M+H]$^+$.

$^1$H NMR (400 MHz, DMSO-d$_6$) δ 9.83 (s, 1H), 8.69 (s, 1H), 8.59 (s, 1H), 8.32 (s, 1H), 8.20 (d, J=4.0 Hz, 1H), 7.68-7.61 (dd, J=14.4, 8.4 Hz, 4H), 7.41-7.39 (t, J=4.4 Hz, 1H), 5.01 (d, J=3.6 Hz, 2H), 3.20 (s, 3H), 2.76 (d, J=4.0 Hz, 3H).

Example 3 Synthesis of N-(trideuteromethyl)-4-((4-(((3-(N-deuteromethylmethane sulfonamido) pyrazin-2-yl)methyl)amino)-5-(trifluoromethyl)pyrimidin-2-yl)amino)benzamide (compound 3)

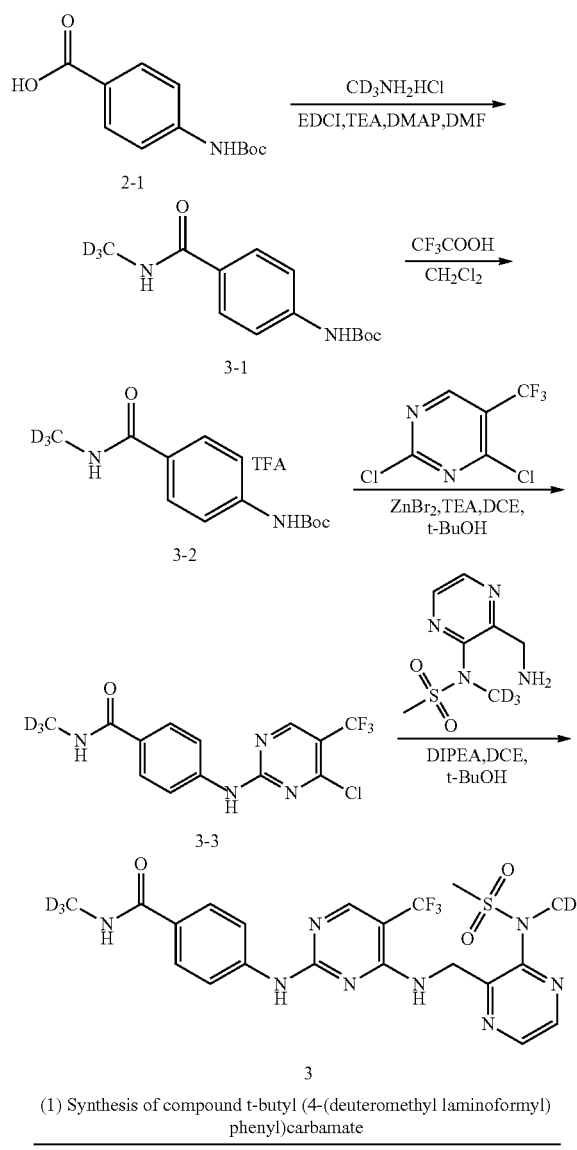

(1) Synthesis of compound t-butyl (4-(deuteromethyl laminoformyl) phenyl)carbamate

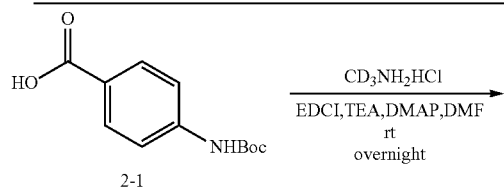

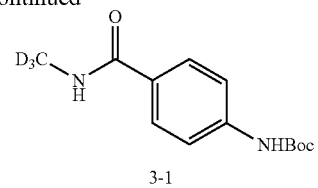

4-((t-Butoxycarbonyl)amino)benzoic acid (1.1 g, 4.64 mmol) was weighed and placed in a 100 mL single-neck round bottom flask, to which was added 20 mL DMF, and stirred at room temperature. Then, EDCI (1.3 g, 6.96 mmol), TEA (1.2 g, 11.6 mmol), deuterated methylamine hydrochloride (327.2 mg, 4.64 mmol), and DMAP (28 mg, 0.23 mmol) were sequentially added to the system. After that, the system was stirred and reacted overnight at room temperature. On the next day, when disappearance of raw materials was monitored, ethyl acetate (30 mL) and water (20 mL) were added to the system, stirred vigorously, and stood for layers separation. The aqueous phase was back-extracted with ethyl acetate (15 mL*3), and the organic layers were combined, washed with water (15 mL*3) and saturated brine (20 mL), then dried with anhydrous sodium sulfate. The solvent was removed by rotary evaporation to obtain the crude product, which was then separated by column chromatography to obtain t-butyl (4-(deuteromethylaminoformyl)phenyl)carbamate as off-white solid (953 mg, yield 81.2%). MS (ESI) m/z 254.2 [M+H]$^+$.

(2) Synthesis of 4-amino-N-deuteromethylbenzamide trifluoroacetate

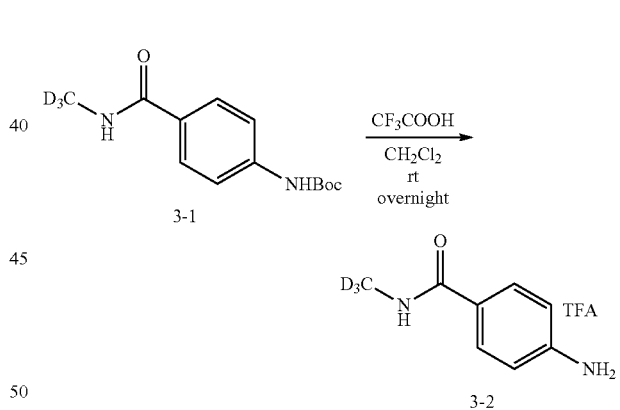

t-Butyl (4-(deuteromethylaminoformyl)phenyl)carbamate (953.0 mg, 3.76 mmol) was weighed and placed in a 50 mL single neck round bottom flask, to which was added dichloromethane (20 mL) and stirred at room temperature. Then, trifluoroacetic acid (5 mL) was added to the system. After addition, the system was stirred and reacted overnight at room temperature. On the next day, the reaction was completed by TLC detection. The reaction solution was concentrated to remove the solvent and excess trifluoroacetic acid, and the residual trifluoroacetic acid in the system was removed by multiple co-steaming with dichloromethane until the system was completely solidified, to obtain 4-amino-N-deuteromethylbenzamide trifluoroacetate (941 mg) as off-white solid, that was directly used in the next step without further purification. MS (ESI) m/z 154.1 [M+H]$^+$.

(3) Synthesis of Compound 4-((4-chloro-5-(trifluoromethyl)pyrimidin-2-yl)amino)-N-deuteromethylbenzamide

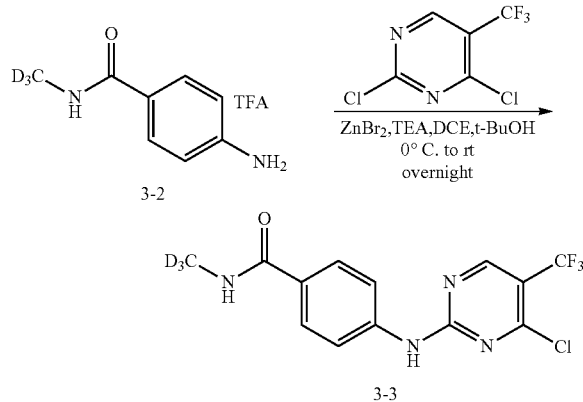

2,4-Dichloro-5-(trifluoromethyl)pyrimidine (891.8 mg, 4.11 mmol) was weighed and placed in a 100 mL single neck round bottom flask, to which were added 1,2-dichloroethane (10 mL) and t-butanol (10 mL), and stirred at room temperature to make the solution become clear. Then, the system was transferred in an ice-water bath to continue cooling and stirring. After 15 min, zinc bromide (2.3 g, 10.71 mmol) was added to the system. After addition, the system was still kept in the ice water bath and stirred for 30 min. Then, 4-amino-N-deuteromethylbenzamide trifluoroacetate and triethylamine (1.2 g, 11.41 mmol) synthesized in the previous step were added to the system. After addition, the ice bath was removed, and the system was stirred and reacted overnight at room temperature. On the next day, the reaction was completed by detection, and after removing the solvent by rotary evaporation, ethyl acetate (50 mL) and water (20 mL) were added to the system. The reaction was stirred vigorously, and stood for layers separation. The aqueous layer was back-extracted with ethyl acetate (20 mL*3), and the organic phases were combined, washed successively with water (20 mL*3) and saturated brine (20 mL), dried with anhydrous sodium sulfate, and concentrated under reduced pressure to obtain a crude product, which was then separated by column chromatography to obtain 4-((4-chloro-5-(trifluoromethyl)pyrimidin-2-yl)amino)-N-deuteromethylbenzamide as off-white solid (467 mg, yield 39.2%). MS (ESI) m/z 334.0 [M+H]$^+$.

(4) Synthesis of Compound N-deuteromethyl-4-((4-(((3-(N-deuteromethylmethanesulfonamido)pyrazin-2-yl)methyl)amino)-5-(trifluoromethyl)pyrimidin-2-yl)amino)benzamide

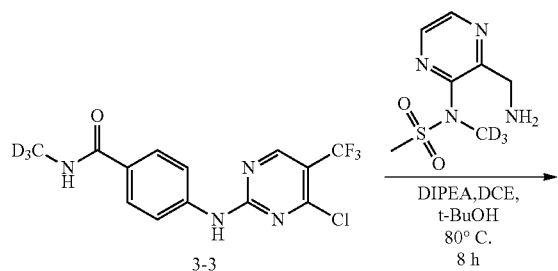

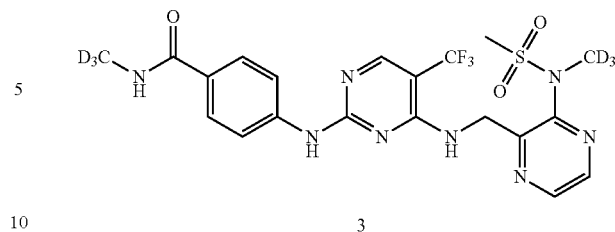

To a 25 mL single-neck round bottom flask containing N-(3-(aminomethyl)pyrazin-2-yl)-N-deuteromethylmethanesulfonamide (43.8 mg, 0.20 mmol), were added 1,2-dichloroethane (3 mL) and t-butanol (3 mL), and stirred at room temperature to make the solution become clear. Then, 4-((4-chloro-5-(trifluoromethyl)pyrimidin-2-yl)amino)-N-deuteromethylbenzamide (66.7 mg, 0.20 mmol) and diisopropylethylamine (77.6 mg, 0.60 mmol) were successively added to the system, and after addition, the system was transferred to an oil bath at 80° C. and refluxed for reaction. After 8 h, disappearance of raw materials was detected by TLC. After heating was removed, and the system was cooled to room temperature, the solvent was removed by rotary evaporation to obtain a crude product, which was then separated and purified by Prep-TLC to obtain N-deuteromethyl-4-((4-(((3-(N-deuteromethylmethanesulfonamido)pyrazin-2-yl)methyl)amino)-5-(trifluoromethyl)pyrimidin-2-yl)amino)benzamide as off-white solid (35.5 mg, yield 34.4%). MS (ESI) m/z 517.2 [M+H]$^+$.

$^1$H NMR (400 MHz, DMSO-$d_6$) δ 9.83 (s, 1H), 8.69 (d, J=2.8 Hz, 1H), 8.58 (d, J=2.4 Hz, 1H), 8.31 (s, 1H), 8.17 (s, 1H), 7.67-7.60 (dd, J=15.4, 8.6 Hz, 4H), 7.42-7.39 (t, J=5.2 Hz, 1H), 5.00 (d, J=4.8 Hz, 2H), 3.20 (s, 3H).

Example 4 Synthesis of N-deuteromethyl-4-((4-(((3-(N-deuteromethylmethanesulfonamido)pyrazin-2-yl)deuteromethyl)amino)-5-(trifluoromethyl)pyrimidin-2-yl)amino)benzamide (compound 5)

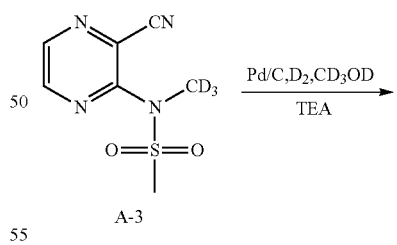

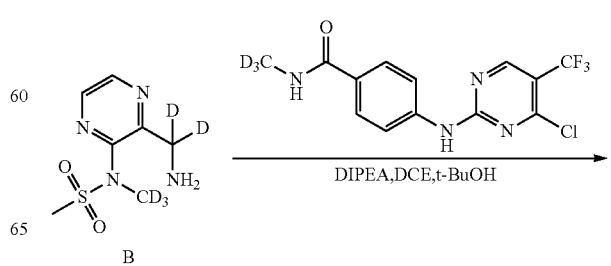

-continued

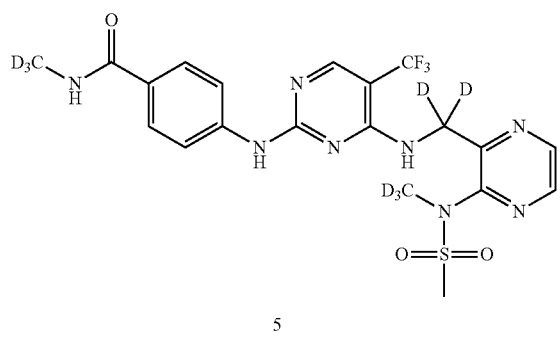

5

(1) Synthesis of Compound N-(3-(aminodeuteromethyl)pyrazin-2-yl)-N-deuteromethyl methanesulfonamide

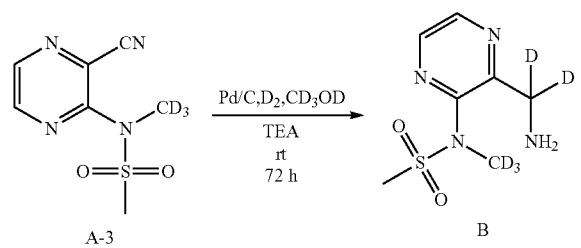

N-(3-cyanopyrazin-2-yl)-N-deuteromethylmethanesulfonamide (100.0 mg, 0.46 mmol) was weighed and placed in a 25 mL single-neck round bottom flask, to which were added 5 mL deuterated methanol, and stirred at room temperature to make the solution become clear. Then, wet palladium carbon (20.0 mg) and triethylamine (188.2 mg, 1.86 mmol) were successively added to the system, and the system was subjected to hydrogen replacement operation, that was repeated ten times. After that, the system was stirred and reacted at room temperature. After 72 h, the reaction was completed by detection. The system was subjected to suction filtration, and the filter cake was rinsed with deuterated methanol (10 mL) several times in small amounts. The filtrate was combined, concentrated under reduced pressure to remove the solvent, to obtain N-(3-(aminodeuteromethyl)pyrazin-2-yl)-N-deuteromethylmethanesulfonamide as light yellow-brown oily liquid, which was directly used in the next step without further purification. MS (ESI) m/z 222.2 [M+H]$^+$.

(2) Synthesis of Compound N-deuteromethyl-4-((4-(((3-(N-deuteromethylmethanesulfonamido)pyrazin-2-yl)deuteromethyl)amino)-5-(trifluoromethyl)pyrimidin-2-yl)amino)benzamide

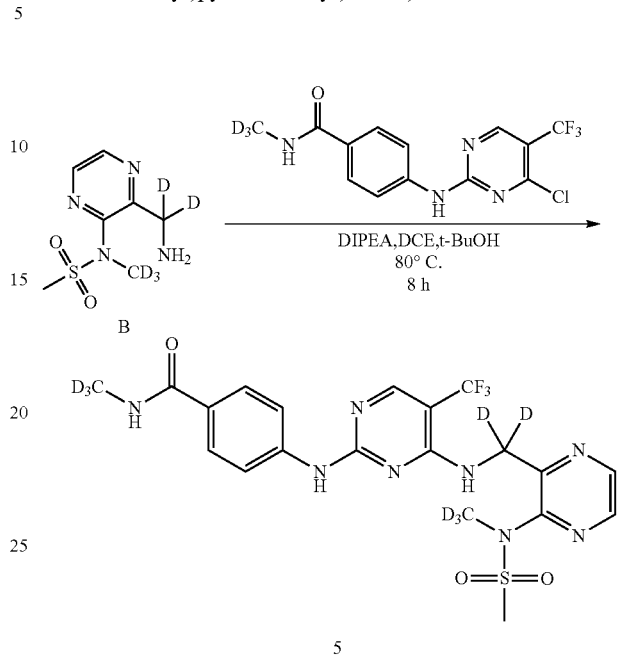

To a 25 mL single-neck round bottom flask containing N-(3-(aminodeuteromethyl)pyrazin-2-yl)-N-deuteromethylmethanesulfonamide (22.1 mg, 0.10 mmol), were added 1,2-dichloroethane (2 mL) and t-butanol (2 mL), and stirred at room temperature to make the solution become clear. Then, 4-((4-chloro-5-(trifluoromethyl)pyrimidin-2-yl)amino)-N-deuteromethylbenzamide (33.4 mg, 0.10 mmol) and diisopropylethylamine (30.6 mg, 0.30 mmol) were successively added to the system, and after addition, the system was transferred to an oil bath at 80° C. and refluxed for reaction. After 8 h, disappearance of raw materials was detected by TLC. After heating was removed, and the system was cooled to room temperature, the solvent was removed by rotary evaporation to obtain a crude product, which was then separated and purified by Prep-TLC to obtain N-deuteromethyl-4-((4-(((3-(N-deuteromethylmethanesulfonamido)pyrazin-2-yl)methyl)amino)-5-(trifluoromethyl)pyrimidin-2-yl)amino)benzamide as off-white solid (8.1 mg, yield 15.6%). MS (ESI) m/z 519.2 [M+H]$^+$. $^1$H NMR (400 MHz, DMSO-d$_6$) δ 9.83 (s, 1H), 8.69 (d, J=2.0 Hz, 1H), 8.58 (d, J=2.4 Hz, 1H), 8.31 (s, 1H), 8.17 (s, 1H), 7.67-7.61 (dd, J=15.2, 8.8 Hz, 4H), 7.39 (s, 1H), 3.20 (s, 3H).

Using the following compounds as raw materials, according to the similar synthetic methods of compounds 1-3, 5 and compound 3-3, compounds 4 and 6-18 of the present invention were prepared: compound A, 2-3, B, 2-4, 3-3, N-(3-(aminomethyl)pyrazin-2-yl)-N-methylmethanesulfonamide (Reference: PCT Int. Appl., 2008129380), N-methylmethanesulfonamide, N-trideuteromethylmethanesulfonamide, 2,4-dichloro-5-(trifluoromethyl)pyrimidine, 4-amino-3,5-dideuterobenzoic acid (Reference: Journal of Labelled Compounds and Radiopharmaceuticals, 53(11-12), 668-673; 2010), 4-amino-2,6-dideuterobenzoic acid (Reference: Journal of Labelled Compounds and Radiopharmaceuticals, 53(11-12), 668-673; 2010).

The beneficial effect of the present invention was illustrated by experimental examples.

Experimental Example 1 Experiment on Metabolic Stability in Liver Microsomes

Step 1. The mother solution was prepared according to the component ratio in Table 1 below:

TABLE 1

Preparation of mother solution

| Reagents | Concentration | Volume | Final concentration |
|---|---|---|---|
| Phosphate buffer | 200 mM | 200 μL | 100 mM |
| high pure water | — | 106 μL | — |
| MgCl₂ solution | 50 mM | 40 μL | 5 mM |

Step 2: Two experiments were carried out as follows:

A) Adding reduced coenzyme II (NADPH): 20 mg/mL liver microsomes (10 μL) and 10 mM NADPH (40 μL) were added into the incubation experiment. The final concentrations of liver microsomes and NADPH were 0.5 mg/mL and 1 mM, respectively.

B) Without NADPH: 20 mg/mL liver microsomes (10 μL) and high pure water (40 μL) were added into the incubation experiment. The final concentration of liver microsomes was 0.5 mg/mL.

Step 3: The reaction began after adding 200 μM positive control (4 μL) or test compound. The positive control was verapamil in this experiment. The final concentration of the test compound was 2 μM.

Step 4: At the time points 0 min, 15 min, 30 min, 45 min, and 60 min, 50 μL solution was sampled from each reaction solution. Acetonitrile (4× volumes of reaction solution) and IS (100 nM alprazolam, 200 nM labetalol, 200 nM caffeine, and 2 μM ketoprofen) were added to the reaction solution. The sample was centrifuged at 3220 g gravity for 40 min. 100 μL high pure water was added into 100 μL supernatant and analyzed by LC-MS/MS.

Step 5: Data analysis: the peak area was determined from the extracted ion chromatogram. The slope value k was determined by linear regression of the natural logarithm obtained from the curve between the residual percentage of parent drug and the incubation time.

In vitro half-life (In vitro $t_{1/2}$) was determined by the slope value: in vitro $t_{1/2}$=−(0.63/k In vitro intrinsic clearance (in vitro $CL_{int}$, in L/min/mg) was converted from in vitro half-life $t_{1/2}$ (min) using the following equation (mean value of repeated determinations):

$$\text{in vitro } CL_{int} = \frac{0.693}{t_{1/2}} \times \frac{\text{volume of incubation } (\mu L)}{\text{amount of proteins (mg)}}$$

Scale up intrinsic clearance (Scale up $CL_{int}$, in mL/min/kg) was converted from in vitro half-life $t_1/2$ (min) using the following equation (mean value of repeated determinations):

$$\text{Scale up } CL_{int} = \frac{0.693}{t_{1/2}} \times \frac{\text{volume of incubation } (\mu L)}{\text{amount of proteins (mg)}} \times \text{Scaling Factor}$$

were shown in Table 2.

TABLE 2

The experimental results of metabolic stability in liver microsomes of mouse, rat and human

| | Half life $t_{1/2}$ (min) in mouse liver microsomes | Half life $t_{1/2}$ (min) in rat liver microsomes | Half life $t_{1/2}$ (min) in human liver microsomes |
|---|---|---|---|
| Defactinib | 63 | 94 | 260 |
| Compound 1 | 87 | 151 | 894 |
| Compound 2 | 70 | 47 | 100 |
| Compound 3 | 406 | 370 | 781 |

As shown in above table, the metabolic stability of compounds 1 and 3 of the present invention in the liver microsomes was significantly improved compared with the non-deuterated control compound defactinib, while the metabolic stability of compound 2 in rat and human liver microsomes was slightly worse than that of non-deuterated control compound defatinib, indicating that the compounds of the present invention, especially compounds 1 and 3, had better metabolic stability. Moreover, it was possible for them to have better pharmacokinetics, better safety and efficacy, that will be further confirmed in the following experimental example.

Experimental Example 2 Pharmacokinetics of Compound According to the Present Invention in Rats 1) Experimental Materials and Instruments:

LC-20AD HPLC system, purchased from SHIMADZU company in Japan

API4000 triple quadrupole mass spectrometer, purchased from Applied Biosystem company in USA PhenixWinnolin pharmacokinetic software (version 6.3), purchased from Certara in USA, High-speed frozen centrifuge, purchased from Thermo Fisher Scientific Analytical balance, purchased from Sartorius, SECURA225D-1CN SD rats, purchased from Chengdu Dashuo Experimental Animal Co., Ltd N, N-Dimethylacetamide (DMA) (Sigma)

Carboxymethylcellulose sodium (CMC Na) and heparin, purchased from Chengdu Kelong Chemical Co., Ltd 2) Experimental methods and results Appropriate amount of drug (equivalent to 10 mg of the original drug) was accurately weighed, to which was first added 0.25 ml DMA to dissolve drug, and 0.5% CMC-Na was slowly added to 5 ml, then mixed well with ultrasonic and vortex. 0.2 ml final solution prepared was taken out and stored at −20° C. for concentration determination. Three healthy adult male SD rats (180-250 g) received drugs at 5 ml/kg by gavage after fasting overnight (free drinking water); 0.1 ml blood was collected from retroorbital venous plexus before administration and 0.5, 1, 2, 4, 6, 8, 12 and 24 h after administration, and plasma was separated by centrifugation at 4° C. for 5 min and stored at −20° C. for use. Then, LC/MS/MS method was used to determine the concentration of compounds in plasma.

TABLE 3

| | Pharmacokinetic parameters of the present invention | | | | |
|---|---|---|---|---|---|
| | Pharmacokinetic experiment in rats (PO, 10 mpk) | | | | |
| Compound | Peak hours $t_{max}$ (h) | Peak plasma concentration $C_{max}$(ng/mL) | Exposure dose AUC (ng*h/mL) | Half life $t_{1/2}$ (h) | Retention time $MRT_{inf}$(h) |
| Defactinib | 0.67 | 643 | 1651 | 1.46 | 2.4 |
| Compound 1 | 0.67 | 1220 | 2843 | 1.74 | 2.03 |
| Compound 3 | 1.67 | 971 | 3741 | 2.46 | 3.35 |

As shown in Table 3, compared with the non-deuterated control compound defactinib, the compound of the present invention had higher peak blood drug concentration, higher exposure dose and longer half-life, indicating that the compound provided in the present invention had better pharmacokinetic performance. The compounds of the present invention had a good prospect in the treatment of cancer.

In summary, various deuterated compounds and the salts, hydrates or solvates thereof provided in the invention can be used as FAK inhibitors to prepare anticancer drugs. Moreover, compared with the non-deuterated control compound defactinib, the metabolic stability and pharmacokinetic properties of the compounds according to the present invention were significantly improved, and the application prospect was excellent.

The invention claimed is:

1. A compound of formula (I) or an optical isomer, a pharmaceutically acceptable salt, a hydrate or a solvate thereof:

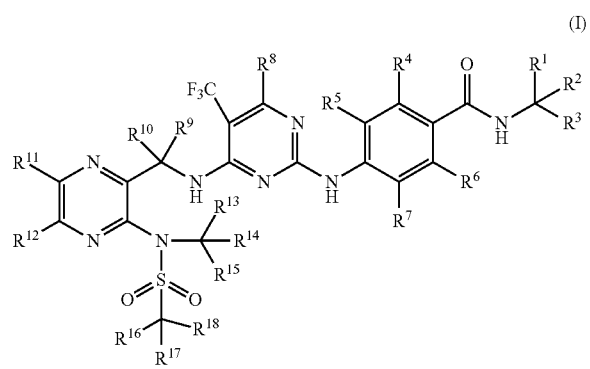

(I)

wherein, $R^1$-$R^{18}$ are each independently selected from hydrogen and deuterium, with the proviso that not all of them are hydrogen at the same time.

2. The compound according to claim 1 or the optical isomer, the pharmaceutically acceptable salt, the hydrate or the solvate thereof, wherein said compound is of formula (II):

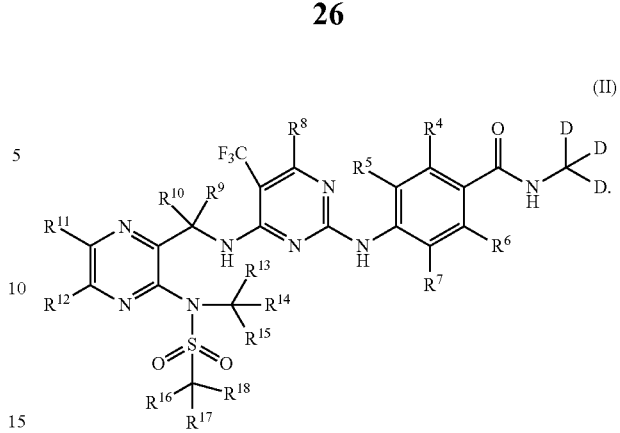

(II)

3. The compound according to claim 1 or the optical isomer, the pharmaceutically acceptable salt, the hydrate or the solvate thereof, wherein said compound is of formula (III):

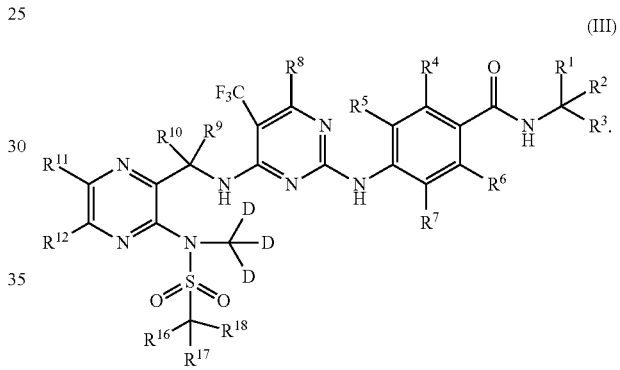

(III)

4. The compound according to claim 1 or the optical isomer, the pharmaceutically acceptable salt, the hydrate or the solvate thereof, wherein said compound is of formula (IV):

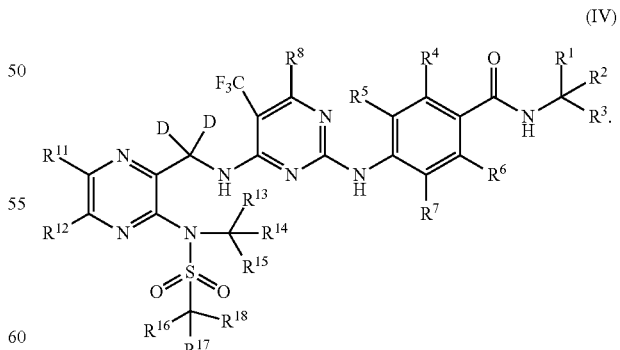

(IV)

5. The compound according to claim 1 or the optical isomer, the pharmaceutically acceptable salt, the hydrate or the solvate thereof, wherein said compound is of formula (V):

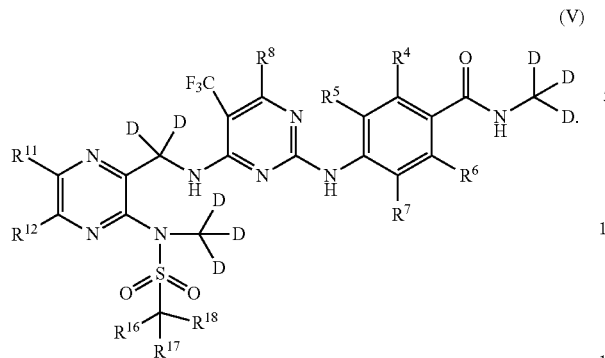
6. The compound according to claim 1 or the optical isomer, the pharmaceutically acceptable salt, the hydrate or the solvate thereof, wherein said compound is one of the following compounds:
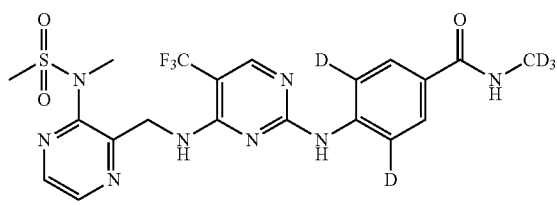
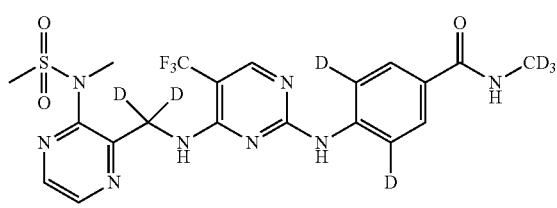
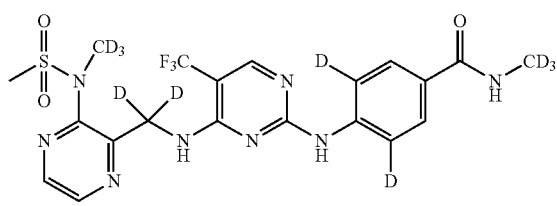
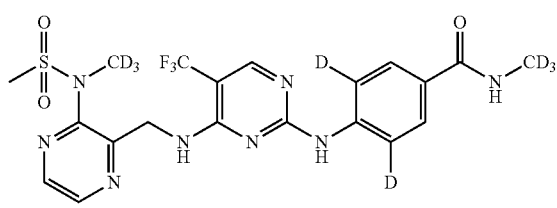
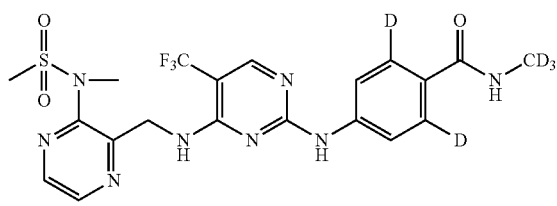
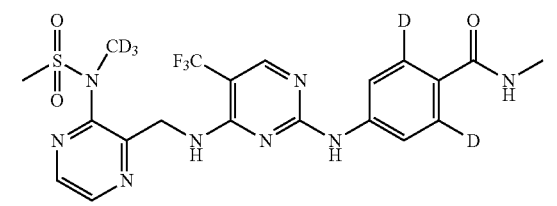
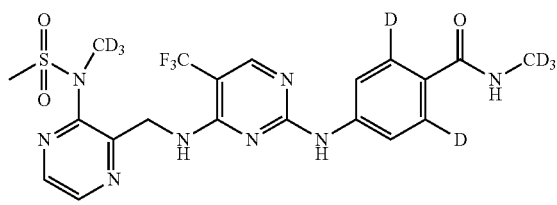

13

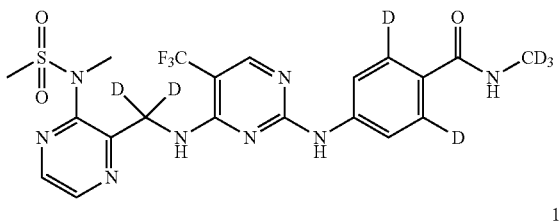

14

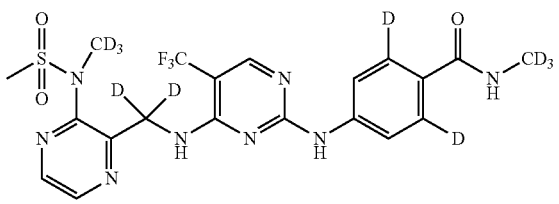

15

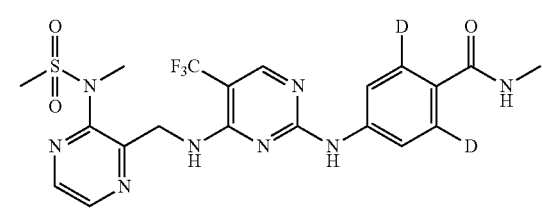

16

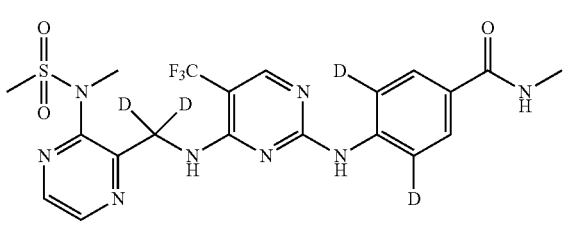

17

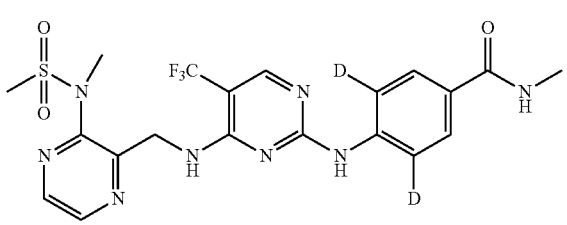

18

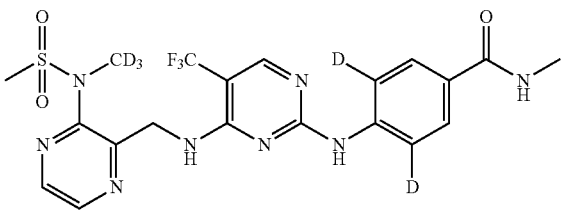

7. The compound according to claim 1 or the optical isomer, the pharmaceutically acceptable salt, the hydrate or the solvate thereof, wherein said pharmaceutically acceptable salt is phosphate, d-camphorsulfonate, hydrochloride, hydrobromide, hydrofluoride, sulfate, nitrate, formate, acetate, propionate, oxalate, malonate, succinate, fumarate, maleate, lactate, malate, tartrate, citrate, picrate, methanesulfonate, besylate, benzenesulfonate, aspartate or glutamate of the compound.

8. A method for treatment of cancers, comprising administering to a subject in need thereof an effective amount of the compound according to claim 1 or the optical isomer, the pharmaceutically acceptable salt, the hydrate or the solvate thereof.

9. The method according to claim 8, wherein the cancer is selected from pancreatic cancer, solid tumor, non-small cell lung cancer, mesothelioma, and ovarian cancer.

10. A method for inhibiting FAK, comprising administering to a subject in need thereof an effective amount of the compound according to claim 1 or the optical isomer, the pharmaceutically acceptable salt, the hydrate or the solvate thereof.

11. A pharmaceutical composition, comprising the compound according to claim 1 or the optical isomer, the pharmaceutically acceptable salt, the hydrate or the solvate as active ingredients, with addition of pharmaceutically acceptable excipients.

12. The compound according to claim 7 or the optical isomer, the pharmaceutically acceptable salt, the hydrate or the solvate thereof, wherein said pharmaceutically acceptable salt is the hydrochloride of the compound.

\* \* \* \* \*